(12) United States Patent
Singh et al.

(10) Patent No.: US 6,187,747 B1
(45) Date of Patent: *Feb. 13, 2001

(54) PHARMACEUTICAL COMPOSITION COMPRISING CYCLOSPORIN

(75) Inventors: Amarjit Singh; Rajesh Jain, both of New Delhi (IN)

(73) Assignee: Panacea Biotech Limited, New Delhi (IN)

( * ) Notice: Under 35 U.S.C. 154(b), the term of this patent shall be extended for 0 days.

This patent is subject to a terminal disclaimer.

(21) Appl. No.: 09/329,602

(22) Filed: Jun. 10, 1999

Related U.S. Application Data

(63) Continuation-in-part of application No. 09/136,663, filed on Aug. 19, 1998, now Pat. No. 6,008,191, which is a continuation-in-part of application No. 09/094,267, filed on Jun. 9, 1998, now Pat. No. 5,945,398.

(30) Foreign Application Priority Data

Sep. 8, 1997 (IN) .............................................. 2532/Del/97

(51) Int. Cl.⁷ ............................ A61K 38/00; A61K 9/00; A61K 38/12; A61K 39/00
(52) U.S. Cl. ............................. 514/11; 514/9; 530/317; 424/400; 424/439; 424/185.1; 426/330.3
(58) Field of Search ........................ 514/9, 11; 530/317; 424/185.1, 400, 439; 426/330.3

(56) References Cited

U.S. PATENT DOCUMENTS

| | | | |
|---|---|---|---|
| 3,288,824 | 11/1966 | Mahler et al. | 260/410.6 |
| 4,108,985 | 8/1978 | Ruegger et al. | 424/177 |
| 4,210,581 | 7/1980 | Ruegger et al. | 260/112.5 R |
| 4,220,641 | 9/1980 | Traber et al. | 424/177 |
| 4,388,307 | 6/1983 | Cavanak | 424/177 |
| 4,719,239 | 1/1988 | Muller et al. | 514/785 |
| 4,835,002 | 5/1989 | Wolf et al. | 426/590 |
| 4,914,188 | 4/1990 | Durmont et al. | 530/317 |
| 4,990,337 | 2/1991 | Kurihara et al. | 424/427 |
| 4,996,193 | 2/1991 | Hewitt et al. | 514/11 |
| 5,047,396 | 9/1991 | Orbán et al. | 514/11 |
| 5,342,625 | 8/1994 | Hauer et al. | 424/455 |
| 5,389,382 | 2/1995 | List et al. | 424/499 |
| 5,504,068 | 4/1996 | Komiya et al. | 514/11 |
| 5,589,455 | 12/1996 | Woo | 514/11 |
| 5,603,951 | 2/1997 | Woo | 424/455 |
| 5,614,491 | 3/1997 | Walch et al. | 514/11 |
| 5,639,724 | 6/1997 | Cavanak | 514/11 |
| 5,645,856 | 7/1997 | Lacy et al. | 424/455 |
| 5,652,212 | 7/1997 | Cavanak et al. | 514/11 |
| 5,741,512 | 4/1998 | Hauer et al. | 424/450 |
| 5,759,997 | 6/1998 | Cavanak | 514/11 |
| 5,766,629 | 6/1998 | Cho et al. | 424/455 |
| 5,798,333 | 8/1998 | Sherman | 514/11 |
| 5,807,820 | 9/1998 | Elas | 514/11 |
| 5,827,822 | 10/1998 | Floc'h et al. | 514/11 |
| 5,834,017 | 11/1998 | Cho et al. | 424/455 |
| 5,945,398 | * 8/1999 | Singh et al. | 514/11 |
| 6,008,191 | * 12/1999 | Singh et al. | 514/9 |

FOREIGN PATENT DOCUMENTS

| | | |
|---|---|---|
| 895724 | 7/1983 | (BE) . |
| 0694308 | 1/1996 | (EP) . |
| 2015339 | 9/1979 | (GB) . |
| 2098865 | 12/1982 | (GB) . |
| 2228198 | 8/1990 | (GB) . |
| 9320833 | 10/1993 | (WO) . |
| 9423733 | 10/1994 | (WO) . |
| 9511039 | 4/1995 | (WO) . |
| 9522982 | 8/1995 | (WO) . |
| 9613273 | 5/1996 | (WO) . |
| 9748410 | 12/1997 | (WO) . |

OTHER PUBLICATIONS

Chemical Abstracts, vol. 89, No. 89: 117875t (1978).
Chemical Abstracts, No. 92: 64765k (1980).
Chemical Abstracts, vol. 94, No. 94: 327c (1981).
Chemical Abstracts, vol. 95, No. 95: 225610k (1981).
Sokol, R.J., et al. "Improvement of cyclosporin absorption in children after liver transplanatation by means of water-–soluble vitamin E." The Lancet, vol. 338 (Jul. 1991) pp. 212–215.
Bulletin Technique Gattefosse, No. 87 (1994), p. 72.
Bulletin Technique Gattefosse, No. 87 (1994).
Microemulsions: Formulation Guide, Gattefosse, p. 6.
Takada, K., et al., International Journal of Pharmaceutics, vol. 44 (1988) pp. 107–116.
English Abstract of WO 9423733 dated Oct. 27, 1994.
English Abstract of WO 9511039 dated Apr. 27, 1995.

* cited by examiner

Primary Examiner—Avis M. Davenport
(74) Attorney, Agent, or Firm—Ladas & Parry

(57) ABSTRACT

The invention disclosed a homogenous substantially alcohol free composition of Cyclosporin which comprises a Cyclosporin in a hydrophilic carrier medium comprising propylene glycol, esters of propylene glycol with C4 to C12 fatty acids and polyoxyethylene hydrogenated castor oils wherein the ingredients are present in the following ranges, Cyclosporin 1–25% w/w, Propylene Glycol 5–50% w/w, Esters of Propylene Glycol with C4 to C12 fatty acids 10–40% w/w and Polyoxyethylene hydrogenated Castor oils 25–60% w/w.

22 Claims, No Drawings

PHARMACEUTICAL COMPOSITION COMPRISING CYCLOSPORIN

This is a continuation-in-part of application Ser. No. 09/136,663 filed on Aug. 19, 1998 and now U.S. Pat. No. 6,008,191 which is a continuation-in-part of application Ser. No. 09/094,267 filed on Jun. 9, 1998, and now U.S. Pat. No. 5,945,398 claims the benefit thereof and incorporates the same by reference.

The present invention relates to pharmaceutical compositions comprising Cyclosporin as active ingredient. The present invention also relates to novel alcohol free, free flowing, clear and transparent compositions comprising Cyclosporin as an active ingredient. The novel compositions are characterised in having increased bio-availability when the drug is formulated in a solubilised system and also amenable to convenient commercial production.

BACKGROUND OF THE INVENTION

Cyclosporins comprise a class of structurally distinctive, cyclic, poly-N-methylated endecapeptides, commonly possessing pharmacological, in particular immunosuppressive, anti-inflammatory and/or anti-parasitic activity. The first of the Cyclosporins to be isolated was the naturally occurring fungal metabolite Ciclosporin or Cyclosporine, also known as Cyclosporin A and commercially available under several brands. Ciclosporin is the Cyclosporin of formula A.

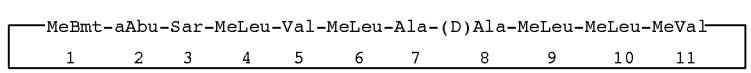

(A)

wherein
MeBmt— represents the N-Methyl-(4R)-4-but-2E-en-1-yl-4-methyl-(L) threonyl residue of formula B.

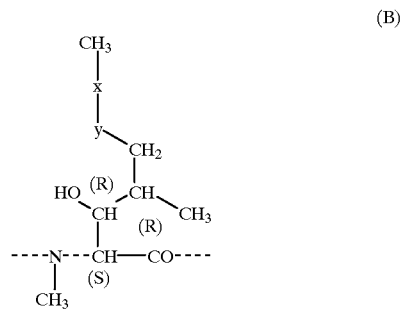

(B)

in which —x—y— is —CH=CH— (trans).

Naturally occurring and semi-synthetic Cyclosporins, their classification, nomenclature etc. are known [c.f Traber et al. 1, Helv. Chim Acta. 60, 1247–1255 (1977): Traber et al. 2, Helv. Chim. Acta. (65 no. 162, 1655–1667 (1982)); Kobel et al., Europ. J. Applied Microbiology and Biotechnology 14, 273–240(1980); and von Wart -burg et al., Progress in allergy , 38,28–45(1986)]. U.S. Pat. Nos 4,108, 985, 4,210,581 and 4,220,641; European Patent Publication Nos. 0034567 and 0056782; International Patent Publication no. WO 86/02080; Wenger 1, Transp. Proc. 15, Suppl. 1; 2230 (1983); Wenger 2, Angew. Chem. Int. Ed., 24,77 (1985); and Wenger 3, Progress in Chemistry of Organic natural Products 50, 123(1986). Other Cyclosporins are known from U.S Pat. Nos. 4,639,434; 4,703,033; 4,764,503, 4,885,276; 5,116,816; 5,122,511; 5,525,590; 5,643,870 and 5,767,069.

So far the primary area of clinical investigation for cyclosporins and in particular, Ciclosporin has been as an immunosuppressive agent, in particular in relation to its application to recipients of organ transplants, e.g. heart, lung, combined heart-lung, liver, kidney, pancreatic, bone-marrow, skin and corneal transplants and, in particular, allogenic organ transplants. In this field Cyclosporins, in particular ciclosporins have achieved a remarkable success. Among all the Cyclosporins, Cyclosporin A (also known as Cyclosporine or Ciclosporin) has established its utility in the area of organ transplant and therapy of autoimmune diseases.

At the same time, applicability of Cyclosporins including Ciclosporin to various autoimmune diseases and to inflammatory conditions, in particular inflammatory conditions with an aetiology including an autoimmune component such as arthritis (for example rheumatoid arthritis, arthritis chronica progrediente and arthritis deformans) and rheumatic diseases, has been intensive and reports and results in vitro, in animal models and in clinical trials are wide-spread in the literature. Specific auto-immune diseases for which Cyclosporin and Ciclosporin therapy has been proposed or applied include, autoimmune hematological disorder (including e.g. hemolytic anaemia, aplastic anaemia, pure red cell anaemia and idiopathic thrombocytopaenia), systemic lupus erythematosus, poly-chondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine opthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthirits and glomerulonephritis (with and without nephrotic syndrome, e.g. including idiopathic nephrotic syndrome or minimal change nephropathy).

Further areas of investigation for cyclosporins include potential applicability as an anti-parasitic, in particular anti-protozoal agent, with possible uses suggested including treatment of malaria, coccidiomycosis and schistosomiasis and, yet more recently, use as an agent for reversing or abrogating anti-neoplastic agent resistance in tumours and the like.

Although Cyclosporin A is the most widely used amongst all the immunosuppresants available so far, it suffers from a serious drawback of poor bio-availability. Cyclosporin blood levels have to be maintained within a specified range to achieve the effective therapy. The required range varies according to the clinical status of the patient.

Because of poor and variable bioavailability daily dosages needed to achieve the desired blood levels need to be varied considerably in the existing dosage forms of Cyclosporin and a concomitant monitoring of blood levels is essential. This adds an additional cost to the therapy.

In order to improve the bio-availibility several attempts have been made to improve formulations of Cyclosporin. The oral dosage forms known in the market (i.e. those employing ethanol, olive oil as carrier medium in conjunction with Labrafil as surfactant (see U.S. Pat. No. 4,388,307) are unpleasant tasting galenic forms. The bio-availability levels using these dosage forms are low and exhibit wide inter-and intra-individual variations. Such dosage forms provide an average absolute bioavailability of ca 30%. Reported variation in bio-availability between subjects varies between a few percent for some patients to as much as 90% or more for others. Also a marked change in bio-availability for individuals with time is frequently observed.

U.S. Pat. No. 4,388,307 also describes a drink solution containing Cyclosporin in a base of Labrafil, Miglyol, Ethanol, Corn/olive oil. However, such preparation suffered from the draw back that it can be presented only as a liquid for dilution in drinking water/fluid before use, otherwise it is very difficult to give an accurate dose. Bioavailability levels achieved using the systems is very low and exhibits wide variations between individuals, individual patient type and even for single individuals at different times during the course of therapy.

Han Gua Patent (Chinese Patent No. 94191895.5) explains the active compound of Cyclosporin, fatty acid sugar ester and diluent carrier having good bio-availability. However, this compound suffers from the drawback that diluent degrades due to hygroscopicity of sugar ester and the stability is not of desired standards, (See also Pharmaceutical Research, Volume 6, No. 11, 1989, P958, "Solid Surfactant Solution of active Ingredients in Sugar Ester" and International Journal of Pharmaceutics, Vol. 92, 1993, P197, "Application of sucrose laurate a new pharmaceutical excipient, in Peroral formulation of Cyclosporin A").

Chinese Patent 9419189.5 having equivalent EP 0702562 describes a powder dosage form of Cycloproin possessing comparatively higher stability and to some extent bio-availability when compared to the earlier formulations. This art describes adsorption of Cyclosporin A with appropriate solvents onto an adsorbent along with a nonionic hydrophillic surfactant. The final product does not contain the solvent as this evaporates during the process of manufacturing. Thus this product does not suffer from the disadvantage arising out of solvent evaporation during shelf life and hence stability problems. The various pharmaceutical surfactants, polyhydric alcohols and solvents are well known to the art. The adsorbent used is Colloidal Silicon Dioxide. The blood level arising out of such product have been compared with the standard formulations as per U.S. Pat. No. 4,388,307 with significant improvement in bioavailability. However, if compared with the micro-emulsion based formulations these formulations do not show any advantage as the drug is adsorbed on solid surface and needs an additional process of dissolution prior to become bioavailable.

The effect of sucrose laurate on the gastrointestinal absorption of Cyclosporine is also described (Lerk-PC; Sucker-H, International Journal of Pharmaceutics; 1993; 92; (May 3); 197–202). The evaluation of the dosage form containing sucrose Laurate was found to enhance the in vitro absorption of Cyclosporine when normal epithelial tissue and Peyer's patch tissue of guinea pigs were used. Compared to the commercially available drinking solution, absorption was raised by a factor of 10. Excess amount of surfactant reduced drug absorption. Despite large excess of Sucrose laurate, the absorption of Cyclosporin was still superior to the drinking solution. Choleic acid was also found to increase absorption by a factor of 5–6. A comparison of the absorption between normal epithelial and Peyer's patch tissues indicated that the absorption by endocytosis does not contribute significantly to the overall absorption of Cyclosporin. It was concluded that preliminary formulation experiments showed that a solid oral dosage form of Cyclosporin could be made using sucrose laurate as an excipient.

Abdallah-HY; Mayersohn-M. Pharmaceutical Research; 1991;8(Apr);518–522 reported several formulations of Cyclosporin were prepared and examined in vitro and in dogs A tablet formulation was then selected for comparison with the commercial oil solution placed in a soft gelatin capsule in a randomized crossover study in dogs. Compared with an intravenous dose of the drug, absolute bioavailability was 46+11.1 and 45+9.9% for the capsules and tablets, respectively. Maximum concentration, time to reach maximum concentration and mean absorption time were not significantly different between the 2 formulations. It was concluded that the tablet formulation of Cyclosporin is equivalent in dogs to the commercial dosage form packed into soft gelatin capsules.

U.S. Pat. No. 505 1402 describes that Cyclosporin may be rendered more soluble by the concomitant administration of α-Cyclodextrin, either separately, but essentially simultaneously or, preferably, in admixture.

U.S. Pat. No. 4,990,337 describes a formulation comprising a Cyclosporin in admixture with at least one mono or diglyceride of a $C_6$–$C_{10}$ fatty acid sufficient to dissolve the Cyclosporin. The resulting solution can then easily be emulsified in water or an aqueous fluid.

Freeze dried liposome mixture containing Cyclosporin has been described in U.S. Pat. No. 4963362. This invention provides a freeze-dried potential liposome mixture having an amphipathic lipid and a Cyclosporin or derivative thereof for use in possible liposome delivery of Cyclosporin into cells. A method to produce the freeze-dried mixture is also desclosed. When reconstituted to yield liposomes in an aqueous medium, substantially all of the Cyclosporin present in the freeze-dried mixture is encapsulated in the liposomes.

Other galenic improvements in Cyclosporin emulsion formulations recorded in prior art are the use of tocopherol derivatives (EP 0724452), tocopheryl polyethyleme glycol carboxylic acid ester (EP 0712631), dimethylisosorbide (EP 0711550, EP 0650721), alkylene polyether or polyester (WO 9423733), emulsion compositions (EP 0694308), anhydromannitol oleylether, lactoglyceride, citroglycerides (EP 656212), phosphatidyl ethanolamine (EP 0651995), as surfactants and stabilizers etc.

Three Patent Applications namely European Patent App. No. 94110184.2, 95117171.9 and PCT/EP95/04 187 describe the use of Dimethylisosorbide as a co-surfactant or a hydrophillic phase along with other ingredients to enhance the absorption of Cyclosporin.

One of the most significant attempt to improve bio-availability of Cyclosporin from its dosage form is the described in U.S. Pat. No. 5,342,625. This art describes use of microemulsion pre-concentrate consisting of a three phase systems i.e. (1) a hydrophilic phase component (2) a lipophilic phase component and (3) a surfactant. Such composition has alcohol as an essential ingredient. Such composition upon dilution with water provides an oil-in-water microemulsion with an average particle size of less than 1000A°. Such an enhanced surface area results in increased bio-availability of Cyclosporin when compared with conventional dosage forms. A comparison of bio-availability from micro-emulsion dosage form (Composition I from U.S. Pat. No. 5,342,625) with the conventional ethanol-oil based dosage form (composition from U.S. Pat. No. 5,342,625), earlier reported in U.S. Pat. No. 4,388,307) has been performed in healthy human volunteers and reported in U.S. Pat. No. 5,342,625. Bio-availability level of 149.0% (±48) is recorded for composition I as compared to composition X (for which bio-availability achieved is set as 100%). The mean AUC levels from composition I were 40% higher when compared to those from composition X but still had a high variation of 20%.

Alcohol is an essential part of composition as is evident from the products available in the market (Sandimun [U.S. Pat. No. 4,388,307] and Neoral [U.S. Pat. No. 5,342,625]) both of which contain Alcohol. Such compositions suffer from severe drawback of instability due to evaporation of a low boiling solvent like Alcohol. This is particularly true as the products are used in home environment, which cannot be precisely controlled with respect to temperature. Although very expensive cumbersome technology (such as cold formed Aluminium/Aluminium Blister packs) is adopted to protect these products, yet the problem of instability is not completely solved. The stability problems are evident from strict storage conditions and usage requirements as declared either on the labels or package inserts of commercial products Sandimun, and Neoral drink solutions and capsules. Some of the examples are:

1. There is a requirement of storage of product below 30° C. at the same time refrigeration is prohibited. This means that a patient using this product in a tropical country need to have an air-conditioned home environment. This is not only a limiting factor in use of this product but sometimes in economically backward countries it may not be possible that every person using the product has an air-conditioned storage area. Sometimes factors like prolong electricity failure and mechanical and electrical defects in air-conditioning system can cause instability problems to these products rendering them unstable for use.

2. There is also an a statement in Packing insert of Sandimun and Neoral drink solutions that "Sandimun Neoral solution should be used within 2 months of opening the bottle and be stored between 15° and 30° C., preferably not below 20° C. for prolonged periods, as it contains oily components of natural origin which tend to solidify at low temperatures. A jelly-like formation may occur below 20° C., which is however reversible at temperatures up to 30° C. Minor flakes or a slight sediment may still be observed. These phenomena do not affect the efficacy and safety of the product, and the dosing by means of the pipette remains accurate." indicating instability problems. U.S. Pat. No. 5,639,724 discloses pharmaceutical compositions comprising Cyclosporin, transesterification product of a natural vegetable oil with glycerol which is exemplified in the specification as MAISINE (transesterification product of corn oil and glycerol) which is an essential component of the compositions. The cyclosporin must be mixed with a transesterfication product of a natural vegetable oil with glycerol. These compositions are not useful as drink solutions because of formation of jelly like lumps, since the transesterfication product is a jelly like substance at room temprature. Such composition also preferably require the use of alcohol. This compositions compares its bioavailability with that of older and inferior compositions based on U.S. Pat. No. 4,388,307 and does not compare bioavailability with a more recently marketed compositions (NEORAL) as defined in U.S. Pat. No. 5,342,625. U.S. Pat. No. 5,639,724 discloses the use of Labrafil as a preferred ingredient to be added to the composition of Cyclosporin and MAISINE for a drink solution. However, this patent does not address the problem of flake like substances formed by the presence of MAISINE even though Labrafil has been added to the composition.

The formulation of emulsion as well as microemulsion present their own technological problems relating to thermodynamic instability. Such problems may be partially solved by presenting the product in a microemulsion preconcentrate form wherein the microemulsification occurs in vivo only. However, such systems may also present variability problems due to wide variations existing in GI tract of patients.

Any person skilled in the art attempting to make compositions without the use of alcohol and without careful and extensive experimentation and study of desired chemicals to be added to Cyclosporin will end with compositions which are highly viscous and which tend to solidify at normal room temperature conditions. Such compositions are undesirable not only due to physical unstability but also that they cannot be formulated as liquids whose dose can be measured exactly under normal conditions.

The major consideration here is the accurate measurement of dose in Cyclosporin which is an essential feature because of the narrow therapeutic condition of the drug i.e. below threshold the organ rejection occurs and above a particular level the drug causes severe toxic reactions.

None of the above mentioned inventions teaches the art of dissolving cyclosporins including Cyclosporin A (which is a water insoluble hydrophobic drug) in a hydrophilic medium. This looks improbable and a person skilled in the art cannot conceive beyond an emulsion and/or a microemulsion.

All the earlier approaches to enhance the bioavailability of Cyclosporin were towards making the drug in a emulsified form (U.S. Pat. No. 4,388,307) or substantially increasing the surface area by converting into microemulsion (U.S. Pat. No. 5,342,625).

Our attempt has been to affect solution of cyclosporin in a hydrophilic environment using micellar concept of a surfactant and a co-surfactant such that such compositions are substantially devoid of fatty materials and hence also devoid of the defects associated with such fatty materials. Compositions according to this invention may be formulated for oral administration including but not limited to drink solutions or formulated as hard or soft gelatin capsules. The capsules may be gelatin or cellulose capsules or two piece hard shell capsules. Drink solution formulations may be diluted with water or aqueous medium and the lipophilic Cyclosporin drug is maintained in a solubilized state, hence making the drug bioavailable in therapeutic concentrations.

It will be most appropriate to formulate Cyclosporin compositions in a way that the drug gets converted into a solubilized system on dilution in vivo. Compositions of the invention when administered orally in the form of a drink solution or soft gelatin capsules get diluted with the gastrointestinal fluids to form micellar solutions such that the hydrophillic end of the surfactant and the cosurfactant are oriented towards hydrophillic environment of gastrointestinal fluid and the drug molecules are entrapped in the hydrophobic portions of the surfactant micelles. Such micellar solubilized systems, when in contact with the mucosa of the gastrointestinal tract, release the drug leading to absorption, thus providing an increased and less variable bioavailibility. The inventors have invented compositions in which hydrophobic drug like Cyclosporin can be dissolved in a hydrophillic medium by careful selection of the hydrophilic medium, surfactants and manner of addition such that a hydrophobic drug can get dissolved in an array of surfactant molecules arranged in a manner that their hydrophilic portions are oriented outside i.e. towards the hydrophilic medium resulting in clear stable solutions based formulations. Such products when they come in contact with biological fluids result in total solubilization of Cyclosporin at molecular levels thereby increasing the surface area of Cyclosporin and such diluted solutions of Cyclosporin are highly bioavailable. Such compositions do not form emulsions on dilution. Such systems will definitely be more uniform and bio-available than microemulsions from where the drug has to partition out of the lipophillic phase for absorption.

Oral solution concentrates are to be diluted prior to intake and are used as start up therapies. These dosage forms provide more flexibility in dosage adjustments to achieve the optimum therapeutic concentrations as desired by the physicians. The second type of dosage forms are unit dosage forms for example capsules, generally soft or hard gelatin capsules or cellulose capsules or two piece hard shell capsules.

SUMMARY OF THE INVENTION

In accordance with the present invention there is described a homogenous substantially alcohol free, composition of Cyclosporin which comprises a Cyclosporin in a hydrophillic carrier medium comprising propylene glycol, esters of propylene glycol with C4 to C12 fatty acids and polyoxyethylene hydrogenated castor oils wherein the ingredients are present in the following range:

| | |
|---|---|
| Cyclosporin | 1–25% w/w |
| Propylene Glycol | 5–50% w/w |
| Esters of propylene glycol with C4 to C12 fatty acids | 10–40% w/w |
| Polyoxyethylene hydrogenated Castor oils | 25–60% w/w |

DETAILED DESCRIPTION OF THE INVENTION

In accordance with the present invention there is described a homogenous substantially alcohol free, composition of Cyclosporin which comprises a Cyclosporin in a hydrophillic carrier medium comprising propylene glycol, esters of propylene glycol with C4 to C12 fatty acids and polyoxyethylene hydrogenated castor oils wherein the ingredients are present in the following range:

| | |
|---|---|
| Cyclosporin | 1–25% w/w |
| Propylene Glycol | 5–50% w/w |
| Esters of propylene glycol with C4 to C12 fatty acids | 10–40% w/w |
| Polyoxyethylene hydrogenated Castor oils | 25–60% w/w |

In another preferred embodiment of the invention the composition further comprises Triacetin or Glycerol triacetate. The glycerol triacetate may be present in the range of 0% to 10% w/w.

In another embodiment of the present invention the composition further comprises Oleic Acid in the range of 0 to 30% w/w. Oleic Acid may partially or completely replace the esters of propylene glycol with C4 to C12 fatty acids.

In another embodiment of the present invention the composition further comprises Antioxidants in the range of 0 to 2% w/w.

The antioxidants can be selected from Butylated Hydroxy Anisole, Bytulated Hydroxy Toluene, Tocopherylacetate or a mixture thereof Other antioxidants may also be used.

In preferred embodiment of the invention is a composition comprising:

| | |
|---|---|
| Cyclosporin | 5–15% w/w |
| Propylene Glycol | 15–45% w/w |
| Esters of propylene glycol with C4 to C12 fatty acids | 15–35% w/w |
| Polyoxyethylene hydrogenated Castor oils | 30–50% w/w |

In another embodiment of the invention the compositions are clear, stable, transparent, easily flowable and easily measurable at a wide range of temperature of 15° to 45° C.

The amount of all of the ingredients of the composition disclosed above equals to 100%.

The systems of the present invention are single phase systems in contrast to emulsion/microemulsions wherein essentially Lipophilic phase is emulsified or microemulsified with Hydrophilic phase using surfactant. The expression "single phase" should be implied to mean a phase wherein the drug is solubilised in Hydrophilic phase using suitable surfactant (s)/ co-surfactant (s).

The cyclosporins used in the compositions may be selected from cyclosporin A, cyclosporin D, cyclosporin G or any other known cyclosporin. It is preferred that cyclosporin A be used.

Dosage forms that are soft gelatin capsules pose unique technology problems when the solutions to be encapsulated are microemulsion preconcentrate. There is a tendency to loose weight due to the migration of materials with free hydroxy groups into the capsule shell thus causing precipitation of drug due to loss of solvent. In the present invention this problem has been solved by adding to the said composition of the invention substantially 10–25% excess of the "carrier medium" thereby compensating for the loss of weight due to migration. At the same time the amount of plasticizers in the capsule shell are reduced by the amount equivalent to the excess carrier medium added in the capsule. The term "base" or "carrier medium" should be implied to mean everything added to the composition except the drug.

The composition is incorporated into the capsule shell by conventional procedures as described in standard texts. ("The theory and practice of Industrial Pharmacy" by Leon Lachman et al. Third edition, LEA AND FEBIGER, USA)

The Soft Gelatin and two piece hard shell Capsules have a very distinct advantage of ease of carrying and administration as compared with oral solutions. These dosage forms hence contribute to a very large segment of commercial market. To aid the filling of the composition into two piece hard shell capsules suitable hydrophilic viscosity imparting agents known in the art, may be added. These may be selected from natural gums like Xanthan gum, Karaya gum, Guar gum, Acacia and the like or semi-synthetic or synthetic polymers like cellulosics e.g. hydroxypropyl cellulose. Hydroxypropylmethyl cellulose, Carboxy methyl cellulose; Acrylates like polymethyl methacrylic acid; carbomers like Carbopol 934, Carbopol 940 (BF Goodrich, USA)

Such compositions of the present invention which are solubilized systems and substantially free of $C_{1-5}$ alkanols such as ethanol are distinctly advantageous over the ones described in U.S. Pat. No. 5,342,625 with respect to manufacturing and distribution in the tropical countries.

It is most beneficial in context of hot tropical countries where absence of $C_{1-5}$ alkanols such as ethanols are more due to evaporation.

Preferably the esters of propylene glycol with C4 to C12 fatty acids include mono-, di- or mono- and di- esters of propylene glycol with C4 to C12 fatty acids. Suitable products include propylene glycol laurate, propylene glycol dicaprylate/dicaprate, propylene glycol dioctanoate, propylene glycol monolaurate and the like. Especially suitable are the products commercially available under the trade names Lauroglycol, Neobee M-20, Capryol and Miglyol-840.

Preferably the Polyoxyethylene hydrogenated castor oil is Polyoxyethylene 40 Hydrogenated Castor oil. Especially suitable is product available under the trade name Cremophor RH 40.

The term "easily measurable" has been used due to the characteristic features of the drug Cyclosporin. Cyclosporin requires accurate dose measurement because of its narrow therapeutic index. Most of the drink solution packs are provided with a pipette or a syringe for accurate dose measurement. This warrants that the solution is a sufficiently thin liquid to permit ease of measurement and not a semi solid mass and also it should be devoid of any flakes, jelly like formations or other sediments which can cause nonhomogeneity in the dose. The composition of our invention possesses all the desired characteristics and hence is easily measurable as far as the dose requirements is concerned. Compositions according to this invention may be formulated as drink solutions or diluted as a drink solution or formulated as soft gelatin capsules or as two piece hard shell capsules.

Several compositions as per this invention with different ranges of ingredients were subjected to commercial production trials and shelf-life stability studies and the inventors were successful in arriving at a composition which was easy to manufacture and stable for long periods of time when tested by accelerated stability studies.

Moreover when tested on healthy human volunteers, the composition(s) of this invention was found to have excellent bio-availability of Cyclosporin and were also found to be bioequivalent with commercial products. The comparative results are collected in Table I & II.

The invention will now be described with reference to the accompanying examples which should not be construed to limit the scope of the invention:

EXAMPLE 1 (PRIOR ART)

| | COMPONENT | AMOUNT |
|---|---|---|
| a) | Cyclosporin | 100 mg (=ca. 10.5%) |
| b) | Maisine | 550 mg (=ca. 57.8%) |
| c) | Labrafil M 2125 | 300 mg (=ca. 33.5%) |
| | TOTAL | 950 mg |

The mixture obtained was a semi-solid mass at room temperature suitable only for soft gelatin capsule formulation.

EXAMPLE 2 (PRIOR ART)

| | COMPONENT | AMOUNT |
|---|---|---|
| a) | Cyclosporin | 100 mg (=ca. 10.5%) |
| b) | Maisine | 490 mg (=ca. 52%) |
| c) | Labrafil M 2125 | 300 mg (=ca. 31.5%) |
| d) | Cremophore RH40 | 60 mg (=ca. 6.3%) |
| | TOTAL | 950 mg |

The mixture obtained was a semi-solid mass at room temperature suitable only for soft gelatin capsule formulation.

EXAMPLE 3 (PRIOR ART)

| | COMPONENT | AMOUNT |
|---|---|---|
| a) | Cyclosporin | 100 mg (=ca. 10.5%) |
| b) | Maisine | 850 mg (=ca. 52%) |
| | TOTAL | 950 mg |

The mixture obtained was a semi-solid mass at room temperature suitable only for soft gelatin capsule formulation.

EXAMPLE 4 (PRIOR ART)

| | COMPONENT | AMOUNT |
|---|---|---|
| a) | Cyclosporin | 100 mg |
| b) | Propylene Glycol | 200 mg |
| c) | Cremophore RH40 | 350 mg |
| d) | Labrafil M1944 | 200 mg |
| e) | Maisine | 150 mg |
| | TOTAL | 1000 mg |

The composition obtained was a clear, homogenous liquid at a temperatures between 25° to 30° C., but at temperatures below 20° C. jelly like flakes separated out. Examples 5 to 12 relate to cyclosporin compositions of the present invention which can be used as a drink solution or can be suitably encapsulated.

EXAMPLE 5

Process for Making Soft Gelatin Capsules of Cyclosporin

The compositions as mentioned in the prior art suffer from a disadvantage of migration of carrier medium comprising solvents containing free —OH groups particularly ethanol into the shell leading to precipitation of drug in the capsules. If alcohol is removed it also leads to precipitation of drug.

To overcome this problem we have surprisingly found in the composition of the present invention that by increasing the amount of carrier medium in the core composition by about 20% at the time of encapsulation and reducing the amount of plasticizers (Sorbitol and Glycerine) in the capsule shell composition by 20% yields soft gelatin capsules which on storage attain equilibrium and remain stable throughout the shelf life as exemplified below:

Batch size: 1,00,000 capsules

| Core Composition | | |
|---|---|---|
| a) | Cyclosporin | 5 kg |
| b) | Carrier Medium* | 55 kg |

*Includes 20% extra carrier medium

| Composition of carrier medium | | |
|---|---|---|
| i) | Propylene Glycol | 10.8 kg |
| ii) | Cremophore RH40 | 24.9 kg |
| iii) | Propylene glycol monolaurate | 18.1 kg |
| iv) | Oleic acid | 1.2 kg |

| Capsule shell composition | | |
|---|---|---|
| i) | Gelatin | 50 kg |
| ii) | Sorbitol | 8 kg |
| iii) | Glycerine | 8 kg |
| iv) | Methyl Paraben | 240 g |
| v) | Propyl Paraben | 140 g |
| vi) | Water | 45 kg |
| vii) | Colour | 400 g |

EXAMPLE 6

| Composition for two piece hard shell capsule | |
|---|---|
| Cyclosporin | 10 gm |
| Propylene Glycol | 18 gm |
| Cremophor RH 40 | 42 gm |
| Propylene glycol laurate | 30 gm |

Propylene Glycol was mixed with Cremophor RH 40 and heated upto 55 to 60° C. and Cyclosporin was dissolved in the resultant. Propylene glycol laurate was then added to the bulk mixture and mixed. The resultant mixture was then filtered. The above composition may be filled in two piece hard shell capsules made up of materials like gelatin or cellulosics (e.g. Hydroxy propyl methyl cellulose based capsules like LICAPS™) using suitably modified machines for filling liquids in two piece hard capsules. The capsules may be sealed using Qualiseal technology. The capsule shell may further comprise plasticizers, colorants, release modifiers, and the like.

EXAMPLE 7

| Cyclosporin | 10 gm |
|---|---|
| Propylene Glycol | 20 gm |
| Cremophor RH 40 | 40 gm |
| Propylene glycol dicaprylate/dicaprate | 30 gm |

Propylene Glycol was mixed with Cremophor RH 40 and heated upto 55 to 60° C. and Cyclosporin was dissolved in the resultant. Propylene glycol dicaprylate/dicaprate was then added to the bulk mixture and mixed. The resultant mixture was then filtered.

EXAMPLE 8

| Cyclosporin | 10 gm |
|---|---|
| Propylene Glycol | 18 gm |
| Cremophor RH 40 | 42 gm |
| Propylene glycol dioctanoate | 30 gm |

Propylene Glycol was mixed with Cremophor RH 40 and heated upto 55 to 60° C. and Cyclosporin was dissolved in the resultant. Propylene glycol dioctanoate was then added to the bulk mixture and mixed. The resultant mixture was then filtered.

EXAMPLE 9

| Cyclosporin | 10 gm |
|---|---|
| Propylene Glycol | 15 gm |
| Cremophor RH 40 | 40 gm |
| Propylene glycol laurate | 17 gm |
| Propylene glycol dicaprylate/dicaprate | 15 gm |
| Triacetin | 3 gm |

Propylene Glycol was mixed with Cremophor RH 40 and heated upto 55 to 60° C. and Cyclosporin was dissolved in the resultant. Propylene glycol laurate was then added to the bulk mixture and mixed. To this was added propylene glycol dicaprylate/dicaprate followed by Triacetin. The resultant mixture was then filtered.

EXAMPLE 10

| Cyclosporin | 10 gm |
|---|---|
| Propylene Glycol | 18 gm |
| Cremophor RH 40 | 42 gm |
| Propylene glycol monolaurate | 30 gm |

Propylene Glycol was mixed with Cremophor RH 40 and heated upto 55 to 60° C. and Cyclosporin was dissolved in the resultant. Propylene glycol ionolaurate was then added to the bulk mixture and mixed. The resultant mixture was then filtered.

EXAMPLE 11

| Cyclosporin | 10 gm |
|---|---|
| Propylene Glycol | 17 gm |
| Cremophor RH 40 | 40 gm |
| Propylene glycol monolaurate | 20 gm |
| Oleic Acid | 10 gm |
| Triacetin | 2.93 gm |
| Tocopheryl Acetate | 0.07 gm |

Propylene Glycol was mixed with Cremophor RH 40 and heated upto 55 to 60° C. and Cyclosporin was dissolved in the resultant. Propylene glycol monolaurate was then added to the bulk mixture and mixed. To this was added Oleic acid, Triacetin and Tocopherylacetate. The resultant mixture was then filtered.

EXAMPLE 12

| Cyclosporin | 10 gm |
|---|---|
| Propylene Glycol | 25 gm |
| Cremophor RH 40 | 40 gm |
| Oleic Acid | 22 gm |
| Triacetin | 2.93 gm |
| Tocopheryl Acetate | 0.07 gm |

Propylene Glycol was mixed with Cremophor RH 40 and heated upto 55 to 60° C. and Cyclosporin was dissolved in the resultant. Oleic Acid was then added to the bulk mixture and mixed. To this was added Triacetin and Tocopherylacetate. The resultant mixture was then filtered.

TABLE I

Plasma Concentration Of Cyclosporine (ng/ml) Following Administration Of a Single Oral Dose Of 2.5 mg/kg Body Wt. Cyclosporine
Name of the preparation: Cyclosporine Composition as per Example 5
Cyclosporine Plasma Concentration (ng/ml)

| Time | Volunteers | | | | | | | | | | | | | |
|---|---|---|---|---|---|---|---|---|---|---|---|---|---|---|
| (Hrs.) | 1 | 2 | 3 | 4 | 5 | 6 | 7 | 8 | 9 | 10 | 11 | 12 | Mean | S.D. |
| 0 | 0 | 0 | 0 | 0 | 0 | 0 | 0 | 0 | 0 | 0 | 0 | 0 | 0 | 0 |
| 1 | 507.02 | 524.93 | 316.14 | 339.72 | 484.29 | 284.79 | 495.09 | 323.50 | 233.15 | 545.52 | 121.57 | 318.47 | 374.50 | 128.58 |
| 2 | 976.15 | 685.17 | 676.67 | 879.30 | 509.18 | 330.00 | 540.17 | 468.40 | 670.99 | 1050.17 | 496.62 | 572.56 | 654.82 | 207.75 |
| 2 | 767.23 | 720.42 | 752.85 | 834.18 | 493.70 | 358.60 | 496.83 | 440.60 | 741.30 | 864.65 | 751.07 | 513.84 | 644.59 | 163.99 |
| 3 | 583.14 | 529.36 | 582.94 | 984.11 | 651.30 | 388.54 | 622.55 | 314.57 | 652.49 | 615.40 | 468.99 | 438.30 | 569.31 | 162.64 |
| 3 | 440.50 | 532.52 | 338.03 | 957.49 | 950.12 | 493.15 | 610.79 | 241.05 | 439.72 | 579.65 | 340.29 | 418.09 | 528.03 | 215.19 |
| 4 | 344.75 | 310.85 | 209.30 | 425.88 | 390.23 | 152.59 | 456.25 | 170.91 | 342.17 | 340.47 | 252.28 | 110.21 | 292.16 | 107.28 |
| 6 | 166.74 | 183.19 | 110.32 | 376.34 | 213.65 | 56.52 | 244.53 | 125.10 | 113.28 | 112.57 | 194.69 | 59.42 | 163.02 | 85.36 |
| 9 | 108.50 | 118.21 | 86.91 | 112.71 | 84.05 | 38.23 | 81.58 | 64.45 | 73.72 | 89.42 | 112.75 | 41.64 | 84.35 | 25.61 |
| 12 | 106.23 | 119.25 | 32.17 | 75.07 | 67.94 | 29.83 | 45.21 | 38.21 | 29.34 | 50.80 | 46.11 | 33.86 | 56.21 | 28.89 |
| 24 | 42.38 | 7.36 | 4.53 | 10.21 | 3.20 | 0.00 | 0.00 | 13.92 | 0.00 | 0.00 | 0.00 | 0.00 | 6.80 | 11.63 |
| Cmax (ng/ml) | 976.15 | 720.42 | 752.85 | 984.11 | 950.12 | 493.15 | 622.55 | 468.54 | 741.30 | 1050.17 | 751.07 | 572.56 | 654.82 | 215.19 |
| Tmax (hrs.) | 2.00 | 2.50 | 2.50 | 3.00 | 3.00 | 3.50 | 3.00 | 2.00 | 2.50 | 2.00 | 2.50 | 2.00 | 2.54 | 0.48 |
| AUC (0–24) | 3459.60 | 3185.80 | 2543.80 | 4709.40 | 3656.3 | 1717.90 | 3510.30 | 2130.60 | 2769.1 | 3294.90 | 2624.30 | 1886.10 | 3024.80 | 1211.20 |

TABLE II

Plasma Concentration Of Cyclosporine (ng/ml) Following Administration Of A Single Oral Dose Of 2.5 mg/kg Body Wt. Cyclosporine
Name of the preparation: SANDIMUN NEORAL
Mfd. by: SANDOZ
Cyclosporine Plasma Concentration (ng/ml)

| Time | Volunteers | | | | | | | | | | | | | |
|---|---|---|---|---|---|---|---|---|---|---|---|---|---|---|
| (Hrs.) | 1 | 2 | 3 | 4 | 5 | 6 | 7 | 8 | 9 | 10 | 11 | 12 | Mean | S.D. |
| 0 | 19.20 | 0.00 | 0.00 | 0.00 | 0.00 | 0.00 | 0.00 | 0.00 | 0.00 | 0.00 | 0.00 | 0.00 | 0.00 | 0.00 |
| 1 | 563.04 | 618.39 | 553.99 | 301.79 | 124.87 | 136.60 | 382.63 | 406.81 | 317.83 | 284.23 | 312.92 | 162.22 | 347.21 | 166.87 |
| 2 | 973.61 | 688.13 | 695.99 | 573.50 | 252.43 | 234.67 | 600.86 | 545.81 | 572.20 | 608.90 | 1005.59 | 609.00 | 613.35 | 230.13 |
| 2 | 799.31 | — | 815.39 | 849.32 | 222.23 | 225.39 | 283.25 | 581.01 | 550.87 | 1113.49 | 975.24 | 629.65 | 586.76 | 344.69 |
| 3 | 871.51 | 648.54 | 564.36 | 654.42 | 292.19 | 147.92 | 292.86 | 395.61 | 389.28 | 958.44 | 1174.33 | 784.34 | 593.24 | 306.57 |
| 3 | 663.07 | 681.19 | 785.13 | 658.20 | 83.34 | 96.44 | 180.02 | 337.68 | 287.32 | 650.95 | — | 476.92 | 403.35 | 274.51 |
| 4 | 479.11 | 508.23 | 203.31 | 220.43 | 126.02 | 155.19 | 167.99 | 258.38 | 131.69 | 374.63 | 413.61 | 390.79 | 301.70 | 242.67 |
| 6 | 244.93 | 219.30 | 150.01 | 315.89 | 54.23 | 100.41 | 155.89 | 155.50 | 73.56 | 209.46 | 196.43 | 236.47 | 176.01 | 76.54 |
| 9 | 173.69 | 239.76 | 138.19 | 187.56 | 45.03 | 30.44 | 213.96 | 61.45 | 46.26 | 135.34 | 114.97 | 98.98 | 119.47 | 64.31 |
| 12 | 89.20 | 185.38 | — | 129.78 | — | 19.41 | 76.61 | 94.40 | — | — | 12.82 | 20.46 | 54.01 | 64.58 |
| 24 | 23.92 | 55.17 | 0.00 | 0.00 | 0.00 | 54.73 | 53.43 | 11.40 | 0.00 | 0.00 | 0.00 | 0.00 | 16.55 | 24.05 |
| Cmax (ng/ml) | 973.61 | 688.13 | 815.39 | 849.32 | 291.19 | 234.67 | 600.86 | 581.01 | 572.2 | 1113.49 | 1174.33 | 784.34 | 723.21 | 278.57 |
| Tmax (hrs.) | 2.50 | 2.00 | 2.00 | 2.00 | 2.50 | 2.00 | 2.00 | 2.00 | 2.00 | 2.00 | 3.00 | 2.50 | 2.20 | 0.40 |
| AUC (0–24) | 4887.00 | 5394.20 | 3136.60 | 4805.00 | 1000.4 | 1527.80 | 2889.20 | 3056.50 | 1730.20 | 3533.40 | 3364.80 | 3118.60 | 3203.6 | 1364.0 |

We claim:

1. A homogenous substantially alcohol free composition of Cyclosporin which comprises Cyclosporin A in a hydrophilic carrier medium comprising propylene glycol, esters of propylene glycol with C4 to C12 fatty acids and polyoxyethylene hydrogentated castor oils wherein the ingredients are present in the following range:

| | |
|---|---|
| Cyclosporin A | 1–25% w/w |
| Propylene Glycol | 5–50% w/w |
| Esters of Propylene glycol with C4 to C12 fatty acids | 10–40% w/w and |
| Polyoxyethylene hydrogenated Castor oils | 25–60% w/w. |

2. A composition as claimed in claim 1 wherein the ingredients are preferably present in the following range:

| | |
|---|---|
| Cyclosporin A | 5–15% w/w |
| Propylene Glycol | 15–45% w/w |
| Esters of propylene glycol with C4 to C12 fatty acids | 15–35% w/w and |
| Polyoxyethylene hydrogenated Castor oils | 30–50% w/w. |

3. A composition as claimed in claim 1, which comprises esters of propylene glycol with C12 fatty acids.

4. A position as claimed in claim 1, which comprises glycerol triacetate or Triacetin.

5. A composition as claimed in claim 4, wherein glycerol triacetate is present in an amount up to 10% w/w.

6. A composition as claimed in claim 1, further comprising oleic acid.

7. A composition as claimed in claim 6, wherein oleic acid is present in an amount up to 30% w/w.

8. A composition as claimed in claim 1, wherein the esters of propylene glycol with C4 to C12 fatty acids are partially or completely replaced with oleic acid.

9. A composition as claimed in claim 1, further comprising one or more antioxidants.

10. A composition as claimed in claim 9, wherein the total amount of antioxidants in the composition is up to 2%.

11. A composition as claimed in claim 9, wherein the antioxidant is butylated hydroxy anisole, butylated hydroxy toluene, tocopherylacetate or a mixture thereof.

12. A position as claimed in claim 1 which can be formulated as a drink solution.

13. A composition as claimed in claim 1 which is free flowing at a temperature of 15 to 45° C.

14. A composition as claimed in claim 4 which is free flowing at a temperature of 15 to 45° C.

15. A composition as claimed in claim 6 which is free flowing at a temperature of 15 to 45° C.

16. A method for treating a cyclosporin indicated condition or symptom comprising administering an effective amount of a composition as claimed in claim 1 to a patient in need thereof.

17. A method as claimed in claim 16 wherein the Cyclosporin indicated condition or symptom is T cell mediated immune process, allograft rejection, inflammation, or autoimmune conditions.

18. A composition as claimed in claim 1, which is formulated as a drink solution, incorporated into a soft gelatin capsule, formulated as a hard gelatin capsule, as a hard cellulose capsule or packed in a suitable device to affect measurable unit dosage dispensing.

19. A drink solution comprising the composition of claim 1.

20. A soft gelatin capsule comprising the composition of claim 1.

21. A hard gelatin capsule comprising the composition of claim 1.

22. A hard cellulose capsule comprising the composition of claim 1.

* * * * *

UNITED STATES PATENT AND TRADEMARK OFFICE
CERTIFICATE OF CORRECTION

PATENT NO. : 6,187,747 B1  
DATED : February 13, 2001  
INVENTOR(S) : Amarjit Singh, et al.

Page 1 of 1

It is certified that error appears in the above-identified patent and that said Letters Patent is hereby corrected as shown below:

<u>Tiel page,</u>
Item [37], "Biotech" should read -- Biotec --.

Signed and Sealed this

Thirtieth Day of October, 2001

*Attest:*

*Attesting Officer*

NICHOLAS P. GODICI
*Acting Director of the United States Patent and Trademark Office*